United States Patent [19]

Kipshidze et al.

[11] Patent Number: 5,437,292

[45] Date of Patent: Aug. 1, 1995

[54] METHOD FOR SEALING BLOOD VESSEL PUNCTURE SITES

[75] Inventors: Nicholas Kipshidze, Bayside; Victor Nikolychik, Whitefish Bay; John E. Baker, Wauwatosa, all of Wis.

[73] Assignee: Bioseal, LLC, Bayside, Wis.

[21] Appl. No.: 155,457

[22] Filed: Nov. 19, 1993

[51] Int. Cl.[6] .............................................. A51B 17/00
[52] U.S. Cl. ...................................... 128/898; 604/53
[58] Field of Search .................... 128/898, 49, 53, 305, 128/30; 604/49, 53, 305, 306; 606/215; 530/381, 382; 435/214

[56] References Cited

U.S. PATENT DOCUMENTS

| | | | |
|---|---|---|---|
| 4,367,749 | 1/1983 | Dudley et al. | 604/53 |
| 4,427,651 | 1/1984 | Stroetman | 530/381 |
| 4,714,460 | 12/1987 | Calderon | 604/53 |
| 5,282,827 | 2/1994 | Kensey | 128/898 |

Primary Examiner—Jerome L. Kruter
Attorney, Agent, or Firm—Dick and Harris

[57] ABSTRACT

A method for percutaneous sealing of punctures in arterial and venous blood vessels is provided. After catheterization of any vessel or organ for diagnostic or interventional procedures or endoscopic or orthopedic procedures involving the intentional puncture and penetration of a vessel wall, or the accidental puncture of a vessel wall, separate solutions containing fibrinogen and thrombin, respectively, are introduced into the tissue surrounding the puncture site. The solutions are allowed to mix forming a semisolid gel at the time of application at the puncture site. The gel further hardens around the site to seal the puncture closed preventing the leakage of blood. Solutions of antibiotics and epinephrine as well as agents that slow clot breakdown may be included in the mixture. An apparatus for accomplishing the method is also disclosed.

17 Claims, 3 Drawing Sheets

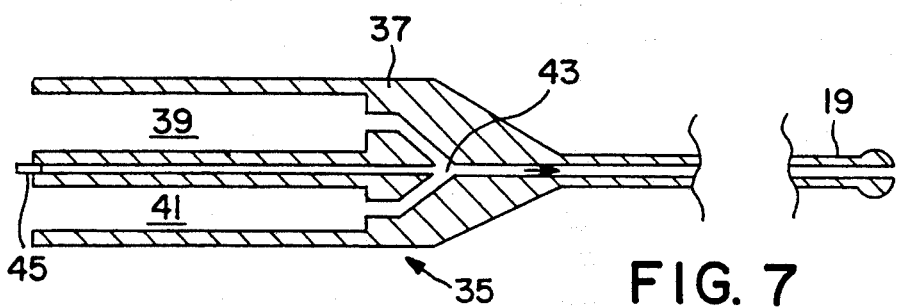
FIG. 7
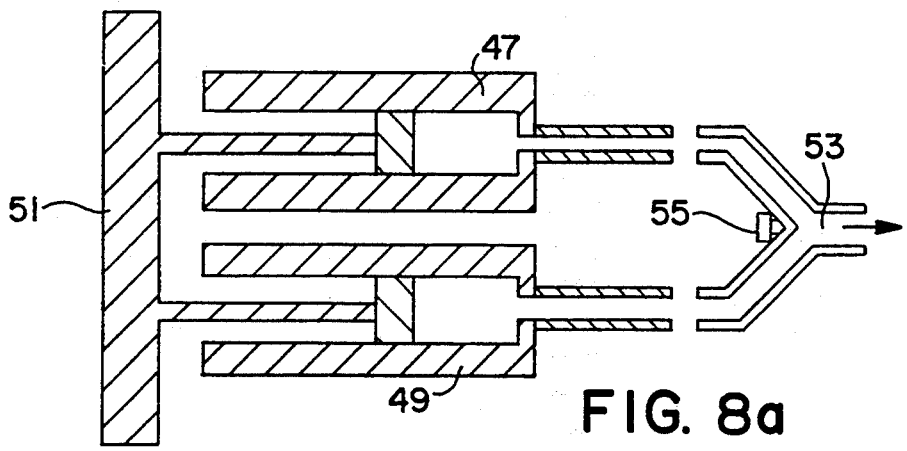
FIG. 8a
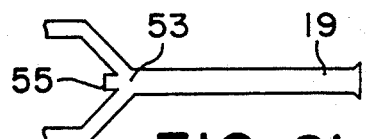
FIG. 8b
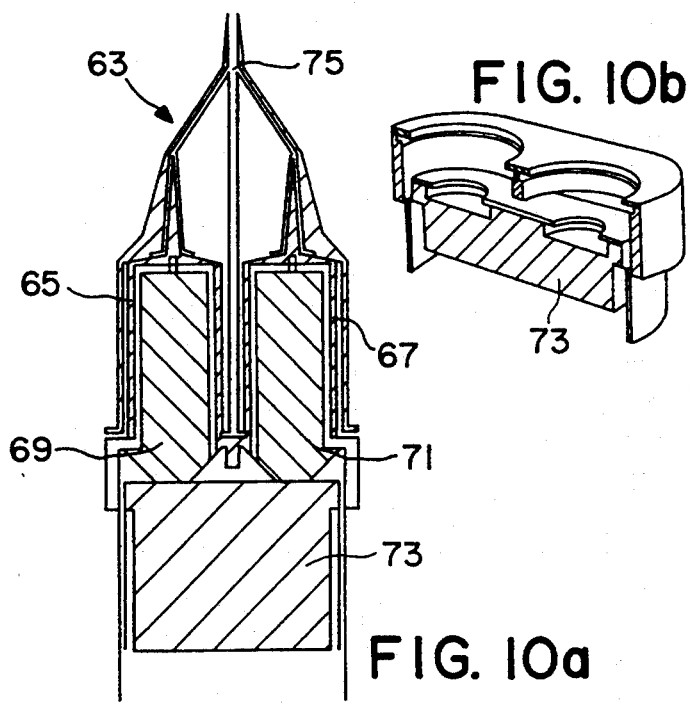
FIG. 10b
FIG. 10a
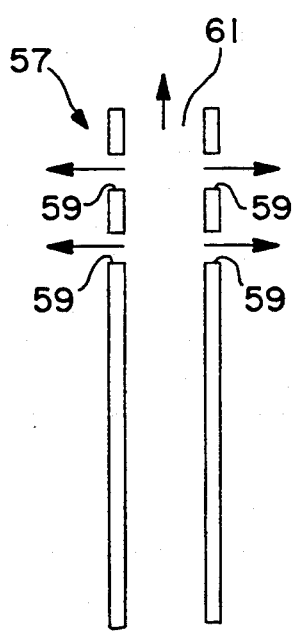
FIG. 9

METHOD FOR SEALING BLOOD VESSEL PUNCTURE SITES

BACKGROUND OF THE INVENTION

The present invention is directed to methods for stopping the leakage of blood from punctures in blood vessels, arterial and venous vessel walls, such as which occur during diagnostic and interventional cardiac and peripheral catheterizations and vascular, endoscopic and orthopedic surgical procedures through induced hemostasis.

The control of bleeding during and after surgical procedures is a critical undertaking, especially if the procedure is performed directly upon or involves the patient's arteries and veins. In particular, well over one million surgical procedures are performed annually which involve the insertion and removal of catheters into and from arteries and veins. The insertion of a typical catheter creates a puncture through the vessel wall and upon removal of the catheter leaves a puncture opening through which blood may escape and leak into the surrounding tissue. Medical personnel are typically required to provide constant and continuing care to a patent who has undergone a procedure involving an arterial or venous puncture to insure that post-operative bleeding is controlled. Unless the puncture site is closed clinical complications may result leading to increased hospital stays with the associated costs.

The control of post-operative leakage of blood from the puncture site has been accomplished in the past in a variety of ways. The most common practice involves application of manual compression directly over the puncture site to slow the blood flow and help hold the puncture closed while natural non-induced clot formation processes take place. However, compression alone can be time consuming, in some cases requiring application of continuous compression on the order of 60–90 minutes, and in some instances may require extension of the patient's stay in hospital. Of course, excessive restriction or interruption of blood flow is undesirable and is to be generally avoided given the risk that undesirable complications may result.

Various blood flow controlling devices (hemostats) have been developed which, although shortening the time required to achieve control (hemostasis), still are time consuming, and can be unnecessarily complicated, with regard to either the procedures or equipment required. Some devices, such as disclosed in Kensey, U.S. Pat. No. 4,744,364, involve the insertion into the arterial or venous vessel of an expandable, biodegradable member which, when deployed, acts to seal the vessel from the inside out. Such devices, however, can have the effect of partially impeding or slowing the flow of blood in the vessel leading to undesirable complications.

Another prior art technique for achieving stopping the leakage of blood is to place a degradable plug directly into the puncture opening, such as a biodegradable collagen plug. Such a procedure is described in the article "Immediate Sealing of Arterial Puncture Sites after Cardiac Catheterization and Coronary Angioplasty Using a Biodegradable Collagen Plug: Results of an International Registry" in the *Journal of the American College of Cardiology*, Vol. 21, No. 4, pp. 851–55. However, as acknowledged in that article, there is a potential for the inadvertent insertion of the collagen plug into the lumen of blood vessel, which could be hazardous to the patient. In order to avoid such insertion, various precautions must be taken, including precise measuring of the distance from the skin surface to the vessel, the use of specially designed oversized applicator devices and plug diameters to prevent passage through the puncture site and entry into the vessel.

Moreover, the typical prior art device serves to seal only a single puncture at a single site upon the vessel whereas often two punctures may be created such as would result when an instrument punctures the vessel wall and travels to and through the vessel wall opposite the initial puncture site. Prior art devices, such as VASOSEAL seal only a single puncture at a time necessitating repeated procedures.

It is an object of the present invention to provide a method for applying a sealant directly to the external wall of an arterial or venous puncture site.

It is a further object of the present invention to provide a simplified method for stopping the flow of blood from a puncture site by sealing a puncture in a blood vessel in a manner which does not require compression or ligation for extended periods of time.

It is another object of the present invention to provide a method for achieving such hemostasis and sealing without requiring an excessive number of special apparatus.

Still another object of the invention is to provide a method for achieving such hemostasis without requiring the insertion of any prosthesis or apparatus into the interior of the vessel itself, or presenting any risk of inadvertent blockage of the vessel through the introduction of a foreign body into the vessel interior.

Another object of the present invention is to provide an apparatus and method capable of sealing two or more vessel punctures at a time without requiring multiple procedures.

Yet another object of the present invention is to provide an apparatus for accomplishing the hemostasis using the method described.

These and other objects of the invention will become apparent in light of the present specification, claims and drawings.

SUMMARY OF THE INVENTION

The present invention comprises a method for accomplishing hemostasis and sealing of a blood vessel having a puncture site therein, the puncture site having been created during a diagnostic and interventional endovascular surgical procedure. Typically, a substantially tubular delivery device is inserted into a patient to a position adjacent a blood vessel, and a surgical device is inserted into the delivery device and into the blood vessel, such as the introduction and subsequent withdrawal of a catheter into an artery.

In particular, the method comprises the steps of:

preparing a supply of a first solution containing fibrinogen;

placing said fibrinogen-containing solution in a first syringe apparatus;

preparing a supply of a second solution containing thrombin;

placing said thrombin-containing solution in a second syringe apparatus;

applying occlusive compression to the blood vessel at a position upstream of the puncture site;

withdrawing the surgical device from the delivery device, while keeping the delivery device in its position adjacent the blood vessel;

releasing the occlusive compression for a brief period of time to enable the puncture site to release an amount of blood into the tissue surrounding the puncture site, sufficient to surround the immediate vicinity of the puncture site, and thereafter reapplying the occlusive compression to stop release of blood from the puncture site;

connecting the first and second syringe apparatus in simultaneous fluid communication with a mixing region and thereafter the delivery device so as to enable mixing of the fibrinogen and thrombin solutions prior to arrival at the puncture site; and actuating the first and second syringe apparatus so as to substantially simultaneously introduce the fibrinogen- and thrombin-containing solutions into the mixing region and thereafter into the delivery device, and into the tissue of the patient adjacent to the puncture site, but not into the blood vessel, so as to enable the mixed solutions to form a gel and thereafter substantially solidify around the puncture site, forming a fibrin matrix, to seal the puncture site against further release of blood.

As an option, after the actuation of the first and second syringe apparatus to introduce the solutions into the delivery device, a deflated, liquid-filled balloon apparatus is introduced into and through the delivery device, so as to position the balloon against the blood vessel adjacent to the puncture site, prior to solidification of the gel formed from the mixed solutions. The balloon is thereafter inflated to press against the blood vessel, and prompt closure of the puncture site and affixation of the gel to the vessel exterior proximate the puncture site.

Preferably, a sufficient amount of fibrinogen is used, to obtain a concentration of fibrinogen in the reagent, of approximately 2.0–15.0 mg/ml. Likewise, a sufficient amount of thrombin is used, to obtain a concentration of thrombin in the reagent, of approximately 10–500 International Units/ml.

The method for accomplishing hemostasis and sealing of a blood vessel may further include the step of adding calcium to one or more of the thrombin and fibrinogen solutions. Factor XIII may also be added to one or more of the thrombin and fibrinogen solutions, to strengthen the fibrin matrix to be formed.

One or more of the following compounds may also be added to one or more of the thrombin and fibrinogen solutions, to prevent or slow the reabsorption of the fibrin matrix: epsilon aminocaproic acid, aminohexanoic acid, aprotinin.

Additionally, a solution of epinephrine may be included with the thrombin and fibrinogen solutions so as to be contained within the gel and applied to the puncture site. Epinephrine serves as a vascular constrictor and temporarily causes the vessel at the puncture site to constrict thereby serving to close the puncture site and assist the gel mixture to seal the puncture. The application of epinephrine provides an additional safety factor in that by further closing the puncture site via constriction of the vessel itself, foreign material is further prevented from entering into the vessel lumen.

In addition to having application in sealing puncture sites associated with cardiac and vascular catheterization procedures, the present invention is deemed useful and applicable to interventional radiology, cardiac procedures including atherectomies, stent implantation, rotablators, thrombolysis therapy, laser angioplasty, valvuloplasty, aortic prosthesis implantation, intraortic balloon pumps, pacemaker implantation and electrophysiology studies as well as in patients with congenital heart disease and those undergoing dialysis and procedures relating to percutaneous extracorporeal circulation. The present invention may be used in both adults and children independent of the age of the vessel to be sealed.

BRIEF DESCRIPTION OF THE DRAWINGS

FIG. 7 is a schematic sectional view showing one embodiment of the combined syringe apparatus according to the present invention;

FIGS. 8a and 8b are schematic sectional views showing another embodiment of the combined syringe apparatus according to the present invention;

FIG. 9 is an enlarged sectional view of the extreme tip of the delivery catheter according to the present invention; and FIGS. 10a and 10b are schematic sectional views of a still further embodiment of the combined syringe apparatus according to the present invention.

DETAILED DESCRIPTION OF THE DRAWINGS

Figure 1:
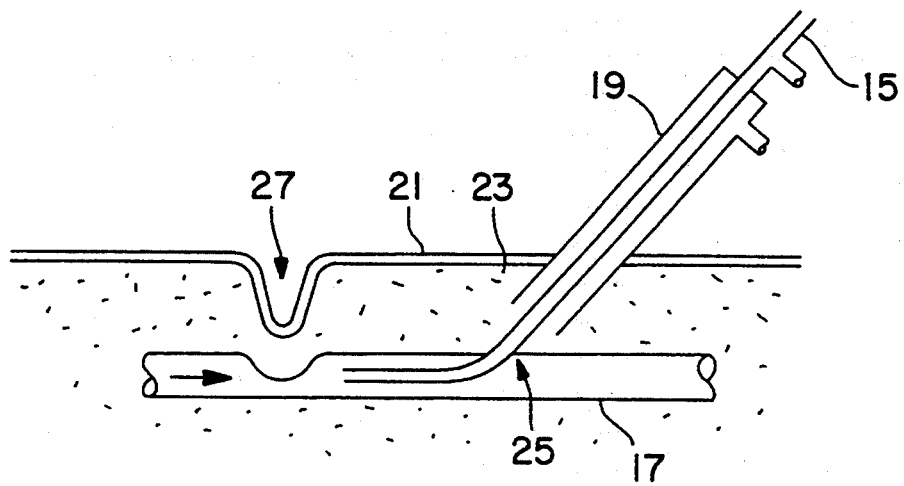
FIG. 1 is a fragmentary sectional view of a blood vessel undergoing a surgical procedure involving catheterization.

While this invention is susceptible of embodiment in many different forms, there is shown in the drawings and will be described herein in detail, several embodiments, with the understanding that the present disclosure is to be considered as an exemplification of the principles of the invention and is not intended to limit the invention to the embodiments illustrated.

FIG. 1 schematically shows a puncture site, at a stage in a surgical procedure when a surgical apparatus, such as catheter 15, is still in position in blood vessel 17, and is insertingly received within delivery catheter 19. Delivery catheter 19 passes through the patient's skin 21, and is positioned in tissue 23, adjacent to puncture site 25, but does not enter and preferably does not contact blood vessel 17. Typically, a guide wire and ultrasound depth detector are used to properly position the delivery catheter. In practice, catheter 17 may have a diameter of 4 French (1 French equals $\frac{1}{3}$ mm), while delivery catheter 19 may have a diameter of 5 French. During the surgical procedure, occlusive pressure is applied, by any of several conventional means, to vessel 17 at a position 27, which is upstream of puncture site 25. During the application of such occlusive pressure, flow of blood through vessel 17 is effectively stopped, and the pressure in vessel 17 may be as low as 0 mm Hg, whereas normal pressure in a non-occluded artery is typically on the order of 100 mm Hg. The normal direction of blood flow in vessel 17 is indicated by the arrow therein.

Prior to removal of catheter 15, a sealant is prepared. The sealant comprises two separate solutions principally of fibrinogen and thrombin, respectively. These compounds may be obtained from conventionally previously prepared forms (cryoprecipitated or chemically precipitated), derived from donor blood, prior to surgical procedure. Alternatively, these compounds may comprise pure sources of fibrinogen wherein cryoprecipitated fibrinogen contains other blood products as well. Using "pure" preparations one is able to achieve high concentrations of fibrinogen. When combined, the two agents react in a manner similar to the final stages of the natural blood clotting process to form a fibrin matrix. Thrombin, a proteolytic enzyme cleaves fibrinogen, a globular protein, into a fibrin monomer and two peptides, fibrinopeptides A and B. These fibrinopeptides act to exert an anticoagulant and vasoconstrictive action on the sealant and exterior of vessel 17, respectively. The fibrin monomer spontaneously polymerizes to form a fibrin matrix that adheres to the puncture site 25 and the surrounding tissue 23, to prevent leakage of blood from vessel 17. The details of the particular composition and properties of the sealant will be discussed later.

Figure 2:
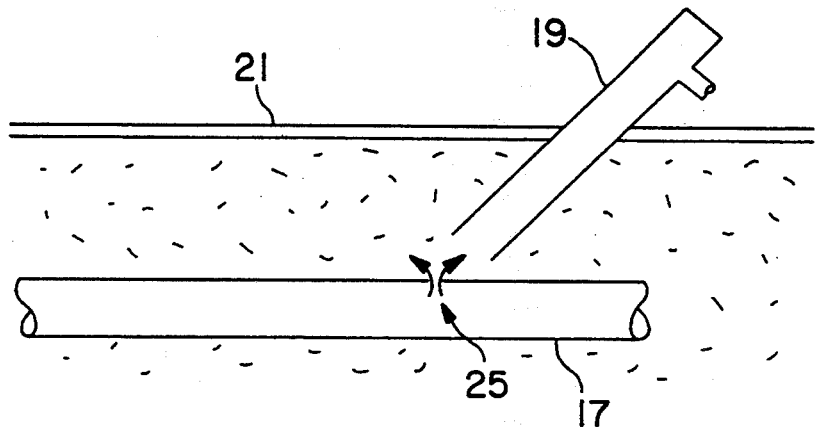
FIG. 2 is a fragmentary sectional view of the blood vessel according to FIG. 1, in which the catheter and occlusive upstream pressure have been removed.

When the surgical procedure is concluded, catheter 17 is removed and the occlusive pressure is released briefly, as indicated in FIG. 2. A preferred duration is 1-2 seconds. A small amount of leakage from puncture site 25 into surrounding tissue 23 accompanies the release of the pressure. However, only enough leakage to sufficiently cover the area in the immediate vicinity of the puncture is desired.

Figure 3:
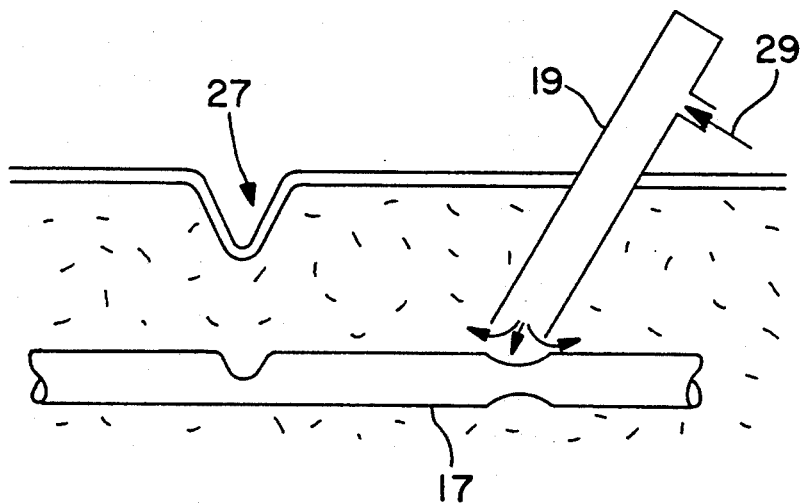
FIG. 3 is fragmentary sectional view of the blood vessel according to FIG. 1, while the sealant solutions are being introduced.

The occlusive pressure is then re-applied, and the sealant 29 is introduced (FIG. 3) into delivery catheter 19, utilizing a combination syringe apparatus, the details of which are described with relation to FIGS. 7-10. Blood vessel 17 is shown slightly constricted, as may arise through the action of certain vasoconstrictor additives, such as epinephrine, which may be included, as desired, into the sealant mix, as described hereafter. By the time that the mixed solutions have entered delivery catheter 19, the thrombin and fibrinogen will have already begun to react, and will have formed a viscous gel or slurry. As the sealant is injected into delivery catheter 19, the back pressure sensed by the combination syringe apparatus is continuously monitored, so as to assure an even and uniform delivery of sealant 29 to the vicinity of puncture site 25. A rapid increase in the back pressure will signify the transition of sealant 29 from its liquid phase to a gel, as the fibrinogen and thrombin react to one another. As a practical matter, due to the increasing viscosity of the sealant material as it travels down delivery catheter 19, toward puncture site 25, there is little significant danger of entry of sealant 29 into blood vessel 17 through puncture site 25, particularly so long as the back pressure is monitored, and does not rise above 80 mm Hg. The temporary release of occlusive pressure, typically 1-2 seconds, permitting a slight leakage of blood from the vessel into the tissue proximate the puncture site provides an additional safety factor in that any component solutions which have not fully reacted prior to reaching the end of delivery catheter 19 will gel upon contact with the leaked blood.

Figure 4:
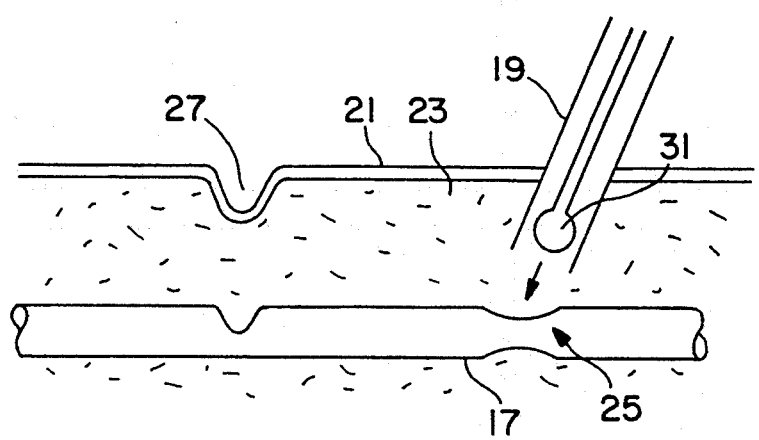
FIG. 4 is a fragmentary sectional view of the blood vessel according to FIG. 1, showing an alternative additional step of inserting an inflatable balloon into the delivery catheter.
Figure 5:
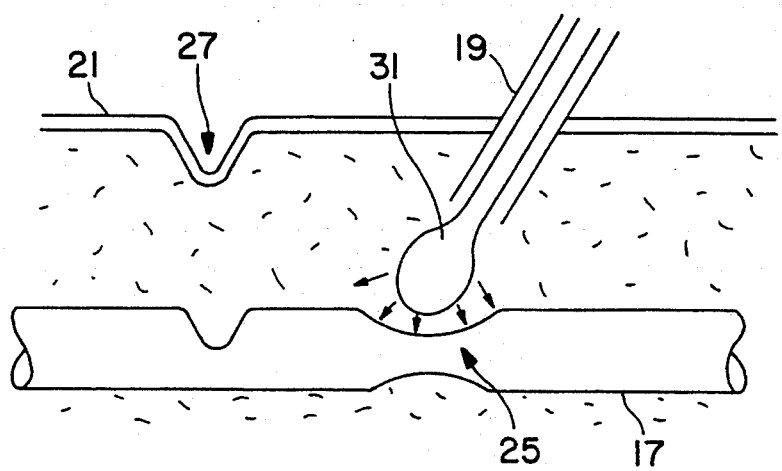
FIG. 5 is a fragmentary sectional view of the blood vessel according to FIG. 4, showing the inflation of the balloon.
Figure 6:
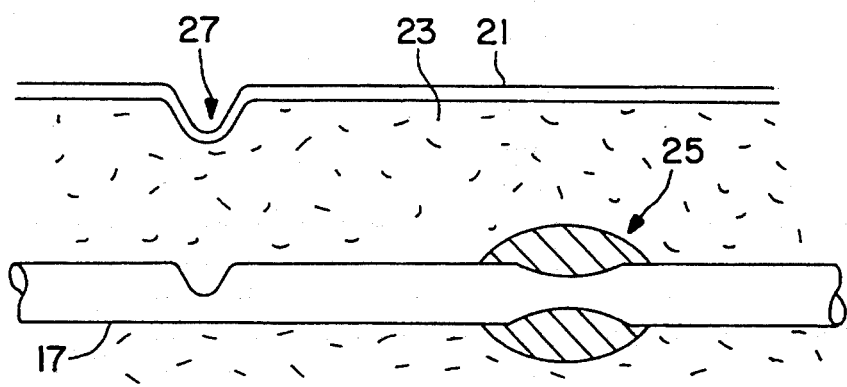
FIG. 6 is a fragmentary sectional view of the blood vessel according to FIG. 1, showing the formation of the fibrin matrix around the puncture site.

After a sufficient volume of sealant 29, preferably an amount of 5-20 cc, has been delivered through delivery catheter 19, delivery catheter 19 may be withdrawn, while occlusive pressure on vessel 17 is maintained, in order to enable sealant 29 to set. Alternatively, in order to facilitate the closure of puncture site 25, as well as the attachment and fixing of some of sealant 29 to the exterior of puncture site 25 in vessel 17, a small, liquid-filled balloon 31 may be inserted into delivery catheter 19 and positioned into tissue 23, above puncture site 25. See. FIGS. 4 and 5. Once in place, balloon 31 may be inflated, and will exert a degree of compression upon vessel 17 at puncture site 25. This compression may be maintained for an optimal period of 5-8 minutes, though the pressure may be applied for somewhat longer or shorter periods, if desired or necessary.

After the appropriate periods of application of pressure via balloon 31 has elapsed (if balloon 31 has been employed), delivery catheter 19 is withdrawn, and the insertion site appropriately closed, manual compression is maintained for 1-8 minutes, to achieve a complete seal of the puncture site. A matrix 33 will form around puncture site 25, forming an effective seal around the puncture, which will substantially prevent leakage from vessel 17 into surrounding tissue 23, while the natural process of self-repair of vessel 17 takes place. Clot 33 will be absorbed by the body gradually, over a period of up to four months.

FIGS. 7-10 disclose various features of several embodiments of combination syringe apparatus contemplated for use in the present method of hemostasis. In FIG. 7 a combination (or gang) syringe apparatus 35 may be fabricated as connectable to delivery catheter 19. Syringe apparatus 35 may include a housing 37, in which are provided two chambers 39 and 41. Chambers 39 and 41 may be configured for receipt of separate syringe cartridges (not shown) in which the separate thrombin and fibrinogen solutions will be contained. The thrombin and fibrinogen cartridges may be depressed simultaneously by jointly connected plungers. The two solutions will be mixed in a mixing chamber 43, and thereafter proceed outward through delivery catheter 19. During the delivery procedure, the back pressure in syringe apparatus 35 and delivery catheter 19 is continually monitored at pressure sensing valve 45, which may be of known configuration.

An alternative configuration is shown in FIGS. 8a and 8b in which separate syringe housings 47 and 49 are provided, which are simultaneously driven by combined plunger 51. The two solutions are mixed in mixing chamber 53, at which position pressure sensor 55 is also situated. From mixing chamber 53, the combined solutions proceed onto delivery catheter 19, as previously described.

Regardless of the configuration of the syringe apparatus, the proper delivery of the rapidly solidifying gel at the puncture site is of great importance. Accordingly, the extreme tip 57 of delivery catheter 19, which is shown in enlarged schematic detail in FIG. 9, is provided with a plurality of side apertures 59 as well as end aperture 61, to ensure that the sealant gel is spread around the puncture site, and to assure that the gel does not leave the delivery catheter 19 in a focused high pressure stream, which could have an undesirable impact upon the puncture site.

While FIGS. 1-7 illustrate the application of the sealant through delivery catheter 19 inserted in a manner providing direct access to the puncture site, it is deemed within the scope of the present invention to utilize a delivery catheter which penetrates the patient's skin at a site remote from the original insertion site, albeit necessitating that a separate hole be made into the skin through which the delivery catheter may be inserted.

A further version of the combined syringe apparatus is shown in FIG. 10, which has a configuration similar to that of FIG. 7, in that a common housing 63 is provided which receives separate syringe cartridges 65 and 67, holding the two solutions. The plungers 69 and 71 are simultaneously propelled by a gang plunger 73 which receives the ends of the separate plungers 69 and 71. Mixing of the solutions occurs in chamber 75.

The performance (i.e., coagulation time) obtained through the foregoing method varies with the relative concentrations of fibrinogen and thrombin in the solutions.

For fibrinogen, the following concentrations and times have been observed:

| Fibrinogen conc. (mg/ml) | Coagulation time (secs.) |
| --- | --- |
| 0.1 | 60 plus/minus 3 |
| 1 | 55 plus/minus 2 |
| 2 | 20 plus/minus 1 |
| 3 | 19 plus/minus 2 |
| 4 | 19 plus/minus 2 |
| 5 | 19 plus/minus 3 |
| 10 | 20 plus/minus 2 |
| 15 | 20 plus/minus 3 |
| 20 | 19 plus/minus 2 |

For thrombin, the concentrations and coagulations times are as follows:

| Thrombin conc. (IU/ml) | Coagulation time (secs.) |
| --- | --- |
| 0.01 | 400 plus/minus 12 |
| 0.1 | 200 plus/minus 7 |
| 1.0 | 50 plus/minus 5 |
| 10 | 20 plus/minus 2 |
| 100 | 19 plus/minus 3 |
| 500 | 20 plus/minus 3 |
| 1000 | 19 plus/minus 2 |
| 1500 | 21 plus/minus 2 |
| 2000 | 20 plus/minus 2 |
| 2500 | 18 plus/minus 3 |
| 3000 | 18 plus/minus 3 |
| 5000 | 19 plus/minus 3 |

According to current observations, it can be seen that once optimal concentrations of approximately 2.0–15 mg/ml of fibrinogen and 10–500 International Units/ml of thrombin have be obtained, the coagulation times are relatively constant at approximately 18–20 seconds.

It may be desirable to add additional compounds to the solutions, in order to achieve specific effects. For example, calcium may be added (in concentrations of approximately 1–5 mmol/l) to Fibrinogen or Thrombin reagent, or Factor XIII (in concentrations of 20–50 µg/ml) may be added to Fibrinogen or Thrombin reagent to increase the strength of the sealant matrix. Addition of these materials does not appear to affect the coagulation time.

Other compounds may be added to prevent or slow the breakdown of the fibrin matrix by the body, after formation. Such compounds may include epsilon aminocaproic acid (concentrations of 0.1–0.001M), aminohexanoic acid (0.1–0.001M), aprotinin (10,000–40,000 International Units), or combinations thereof. The use of previously prepared (as through cryoprecipitation or chemical precipitation) fibrinogen, in contrast to pure sources of Thrombin and Fibrinogen, may affect the reabsorption rates, but without affecting the effectiveness of the matrix formation and puncture sealing. Omission of these compounds does not affect the performance of the matrix, aside from not accelerating the rate of reabsorption of the matrix.

The effect of fibrinolytics and antifibrinolytics upon lysis of the sealant as experienced from six studies per group, data mean±SD, are as set forth in the following chart:

| Composition of Sealant | Lysis time (hours) |
| --- | --- |
| Fibrinogen & thrombin | 12 ± 3 |
| Fibrinogen & thrombin & calcium | 12 ± 3 |
| Fibrinogen & thrombin & Factor XIII | 18 ± 3 |
| Fibrinogen & thrombin & epsilon amino caproic acid | |
| $10^{-1}$ M | 28 ± 4 |
| $10^{-1}$ M | 27 ± 4 |
| $10^{-3}$ M | 10 ± 1 |
| $10^{-4}$ M | 8 ± 1 |
| Fibrinogen & thrombin & amino hexanoic acid | |
| $10^{-1}$ M | 29 ± 3 |
| $10^{-1}$ M | 28 ± 2 |
| $10^{-3}$ M | 27 ± 3 |
| $10^{-4}$ M | 14 ± 1 |
| $10^{-5}$ M | 10 ± 1 |
| Fibrinogen & thrombin & aprotinin IU | |
| 10,000 IU | 22 ± 2 |
| 20,000 IU | 25 ± 3 |
| 30,000 IU | 26 ± 2 |
| 40,000 IU | 26 ± 3 |
| Standard cryoprecipitated Fibrinogen & thrombin | 28 ± 2 |
| Standard cryoprecipitated Fibrinogen & thrombin & epsilon amino caproic acid $10^{-2}$ M amino hexanoic acid $10^{-2}$M | 32 ± 3 |
| | 34 ± 3 |

Other compounds may also be included in the sealant solutions, such as epinephrine, as previously described or antibiotics to prevent or treat infection, such as cefazolin sodium in 50–100 milligrams dosage.

This method and accompanying apparatus may be used in a variety of procedures, including endoscopic and orthopedic surgery, cardiovascular surgery, and so on. An additional benefit from the use of the above-described procedure becomes evident during its use in cardiovascular procedures. During such procedures, the patient is dosed with anticoagulants, such as heparin, aspirin or coumadin, which may effectively neutralize the patient's hemostatic system. It has been observed that the required times for manual compression of the puncture site, after removal of the delivery catheter, are not significantly extended in the presence of such compounds in the patient's system, with compression times of only up to 8 minutes being required.

The length of compression time varies according to the size of the puncture, which in turn varies according to the diameter of the catheter used during the surgical procedure. It has been observed that catheter diameters of 7F required a compression time of 1–4 minutes, while punctures caused by catheters of up to 9F require compression of from 5–10 minutes where blood has been anticoagulated with heparin or coumadin.

Such compression times are believed to be a significant improvement over the times required when other methods of hemostasis are employed, particularly when the patient has been dosed with anticoagulants, such as heparin. For example, manual compression alone has been observed to require from approximately 30 to 65 minutes, the Kensey hemostat has required from approximately 20 to 28 minutes of compression, and the collagen plug method has required from 18 to 25 minutes of compression.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A method for sealing a puncture site in the wall of a blood vessel, the puncture site having been created accidentally, or intentionally during an endovascular or surgical procedure, wherein a substantially tubular percutaneous delivery device is positioned adjacent a blood vessel puncture site without penetrating the vessel, the method comprising the steps of:
    preparing a supply of a first solution containing fibrinogen;
    placing said fibrinogen-containing solution in a first syringe apparatus;
    preparing a supply of a second solution containing thrombin;
    placing said thrombin-containing solution in a second syringe apparatus;
    applying occlusive compression to the blood vessel at a position upstream of the puncture site;
    releasing the occlusive compression for a brief period of time to enable the puncture site to release an amount of blood into the tissue surrounding the puncture site, sufficient to surround the immediate vicinity of the puncture site, and thereafter reapplying the occlusive compression to stop release of blood from the puncture site;
    connecting the first and second syringe apparatus in simultaneous fluid communication with a mixing region and thereafter the delivery device so as to enable mixing of the fibrinogen and thrombin solutions prior to delivery to the puncture site;
    actuating the first and second syringe apparatus so as to substantially simultaneously introduce the fibrinogen- and thrombin-containing solutions into the mixing region to form a gel and thereafter into the delivery device, and into the tissue of the patient adjacent to the puncture site but not into the blood vessel, so as to enable the gel to thereafter substantially solidify around the puncture site and seal the puncture site against further release of blood.

2. The method for sealing the wall of a blood vessel having a puncture site therein according to claim 1, further including the steps of:
    disconnecting said first and second syringe apparatus from the delivery device after introducing the solutions which will form a gel into the tissue adjacent the puncture site;
    introducing a deflated, liquid-filled balloon apparatus into and through the delivery device;
    positioning the balloon apparatus into the tissue above the puncture site;
    inflating the balloon apparatus prior to solidification of the gel formed from the mixed solutions such that the balloon apparatus presses against the gel, and in turn the blood vessel, to prompt closure of the puncture site; and
    deflating and removing the balloon apparatus prior to final solidification of the gel.

3. The method for sealing the wall of a blood vessel having a puncture site therein according to claim 1, wherein a sufficient amount of fibrinogen is used, to obtain a concentration of fibrinogen in the matrix, of approximately 2.0–15.0 mg/ml.

4. The method for sealing the wall of a blood vessel having a puncture site therein according to claim 1, wherein a sufficient amount of thrombin is used, to obtain a concentration of thrombin in the matrix, of approximately 10–500 International Units/ml.

5. The method for sealing the wall of a blood vessel having a puncture site therein according to claim 1, wherein calcium is added to one or more of the thrombin and fibrinogen solutions.

6. The method for sealing the wall of a blood vessel having a puncture site therein according to claim 5, wherein calcium is added to one or more of the thrombin and fibrinogen solutions in concentrations of approximately 1–5 mmol/l.

7. The method for accomplishing hemostasis and sealing of a blood vessel according to claim 1, wherein Factor XIII is added to one or more of the thrombin and fibrinogen solutions.

8. The method for accomplishing hemostasis and sealing of a blood vessel according to claim 7, wherein Factor XIII is added to one or more of the thrombin and fibrinogen solutions in concentrations of approximately 20–50 $\mu$g/ml.

9. The method for sealing the wall of a blood vessel having a puncture site therein according to claim 1, wherein one or more of the following compounds is added to one or more of the thrombin and fibrinogen solutions: epsilon aminocaproic acid, aminohexanoic acid, aprotinin.

10. The method for sealing the wall of a blood vessel having a puncture site therein according to claim 9, wherein said epsilon aminocaproic acid is in concentrations of approximately 0.1–0.001M.

11. The method for sealing the wall of a blood vessel having a puncture site therein according to claim 9, wherein said aminohexanic acid is in concentrations of approximately 0.1–0.001M.

12. The method for sealing the wall of a blood vessel having a puncture site therein according to claim 9, wherein said aprotinin is in concentrations of approximately 10,000–40,000 International Units.

13. The method for sealing the wall of a blood vessel having a puncture site therein according to claim 1, further including the step of monitoring the pressure within said delivery device wherein an increase in pressure serves as an indication that said solutions transition from a liquid to a gel and further to insure that said pressure attributable to said syringe apparatus does not exceed the pressure within the vessel being sealed thereby preventing penetration of said gel into said vessel interior.

14. The method for sealing the wall of a blood vessel having a puncture site therein according to claim 1, wherein a vascular constrictor is added to one or more of the thrombin and fibrinogen solutions.

15. The method for sealing the wall of a blood vessel having a puncture site therein according to claim 14, wherein said vascular constrictor comprises epinephrine which temporarily causes the vessel at the puncture site to constrict thereby serving to facilitate sealing of the puncture site.

16. A method for sealing a puncture site in the wall of a blood vessel, the puncture site having been created accidentally, or intentially during an endovascular or surgical procedure, wherein a substantially tubular percutaneous delivery device is positioned adjacent and external to a blood vessel puncture site, the method comprising the steps of:

mixing a first solution containing fibrinogen with a second solution containing thrombin;

allowing said mixture to interact forming a gel;

applying occlusive compression to the blood vessel at a position upstream of the puncture site;

releasing the occlusive compression for a brief period of time to enable the puncture site to release an amount of blood into the tissue surrounding the puncture site, sufficient to surround the immediate vicinity of the puncture site, and thereafter reapplying the occlusive compression to stop release of blood from the puncture site;

delivering said gel mixture of fibrinogen and thrombin to the tissue of the patient adjacent to the puncture site but not into the blood vessel, so as to enable the gel mixture to thereafter substantially solidify around the puncture site and seal the puncture site against further release of blood.

17. A method for sealing a puncture site in the wall of a blood vessel, the puncture site having been created accidentally, or intentionally during an endovascular or surgical procedure, wherein a substantially tubular percutaneous delivery device is positioned adjacent a blood vessel puncture site without penetrating the vessel, the method comprising the steps of:

preparing a supply of a first solution containing fibrinogen;

placing said fibrinogen-containing solution in a first syringe apparatus;

preparing a supply of a second solution containing thrombin;

placing said thrombin-containing solution in a second syringe apparatus;

applying occlusive compression to the blood vessel at a position upstream of the puncture site;

connecting the first and second syringe apparatus in simultaneous fluid communication with a mixing region and thereafter the delivery device so as to enable mixing of the fibrinogen and thrombin solutions prior to delivery to the puncture site;

actuating the first and second syringe apparatus so as to substantially simultaneously introduce the fibrinogen- and thrombin-containing solutions into the mixing region to form a gel and thereafter into the delivery device, and into the tissue of the patient adjacent to the puncture site but not into the blood vessel, so as to enable the gel to thereafter substantially solidify around the puncture site and seal the puncture site against further release of blood.

* * * * *